US00PP23305P2

(12) United States Plant Patent
Star

(10) Patent No.: US PP23,305 P2
(45) Date of Patent: Jan. 1, 2013

(54) ***ERYNGIUM* PLANT NAMED 'WHITE STAR'**

(50) Latin Name: *Eryngium alpinum*
Varietal Denomination: White Star

(76) Inventor: Jan Star, Rijnsburg (NL)

( * ) Notice: Subject to any disclaimer, the term of this patent is extended or adjusted under 35 U.S.C. 154(b) by 0 days.

(21) Appl. No.: 13/136,893

(22) Filed: Aug. 12, 2011

(51) Int. Cl.
*A01H 5/00* (2006.01)

(52) U.S. Cl. ..... Plt./361

(58) Field of Classification Search ..... Plt./361
See application file for complete search history.

*Primary Examiner* — Kent L Bell
(74) *Attorney, Agent, or Firm* — C. A. Whealy

(57) ABSTRACT

A new and distinct cultivar of *Eryngium* plant named 'White Star', characterized by its upright plant habit; strong thick stems; strong and durable leaves; white-colored flowers on dense flower heads; and good garden performance.

3 Drawing Sheets

Botanical designation: *Eryngium alpinum.*
Cultivar denomination: 'WHITE STAR'.

BACKGROUND OF THE INVENTION

The present invention relates to a new and distinct cultivar of *Eryngium* plant, botanically known as *Eryngium alpinum*, and hereinafter referred to by the name 'White Star'.

The new *Eryngium* plant is a naturally-occurring whole plant mutation of an unnamed selection of *Eryngium alpinum*, not patented. The new *Eryngium* plant was discovered and selected by the Inventor as a single flowering plant from within a population of plants of the parent selection in a controlled outdoor nursery environment in Rijnsburg, The Netherlands in June, 2004.

Asexual reproduction of the new *Eryngium* plant by cuttings in a controlled environment in Rijnsburg, The Netherlands since June, 2004 has shown that the unique features of this new *Eryngium* plant are stable and reproduced true to type in successive generations.

SUMMARY OF THE INVENTION

Plants of the new *Eryngium* have not been observed under all possible environmental conditions. The phenotype may vary somewhat with variations in environment such as temperature and light intensity, without, however, any variance in genotype.

The following traits have been repeatedly observed and are determined to be the unique characteristics of 'White Star'. These characteristics in combination distinguish 'White Star' as a new and distinct cultivar of *Eryngium:*

1. Upright plant habit.
2. Strong thick stems.
3. Strong and durable leaves.
4. White-colored flowers on dense flower heads.
5. Good garden performance.

Plants of the new *Eryngium* differ from plants of the parent selection in the following characteristics:

1. Plants of the new *Eryngium* have lighter-colored and more durable leaves than plants of the parent selection.
2. Plants of the new *Eryngium* and the parent selection differ in flower color as plants of the parent selection have blue-colored flowers.

Plants of the new *Eryngium* can also be compared to plants of the *Eryngium alpinum* 'Sapphire Blue', disclosed in U.S. Plant Pat. No. 11,088. Plants of the new *Eryngium* differ from plants of 'Sapphire Blue' in the following characteristics:

1. Plants of the new *Eryngium* had larger flowers than plants of 'Sapphire Blue'.
2. Plants of the new *Eryngium* and 'Sapphire Blue' differed in flower color as plants of 'Sapphire Blue' had dark violet blue-colored flowers.

BRIEF DESCRIPTION OF THE PHOTOGRAPHS

The accompanying photographs illustrate the overall appearance of the new *Eryngium* plant showing the colors as true as it is reasonably possible to obtain in colored reproductions of this type. Colors in the photographs may differ slightly from the color values cited in the detailed botanical description which accurately describe the colors of the new *Eryngium* plant.

The photograph on the first sheet comprises a side perspective view of a typical flowering plant of 'White Star' grown in a one-gallon container.

The photograph on the second sheet is a close-up view of typical inflorescences of 'White Star'.

The photograph on the third sheet is a close-up view of typical leaves of 'White Star'.

DETAILED BOTANICAL DESCRIPTION

The aforementioned photographs and following observations and measurements describe plants grown during the late spring and early summer in an outdoor nursery in Rijnsburg, The Netherlands under environmental conditions and cultural practices which approximate those generally used in commercial *Eryngium* production. During the production of the plants, day temperatures ranged from 14° C. to 28° C. and night temperatures ranged from 4° C. to 16° C. Plants were one-year old when the photographs and description were taken. In the following description, color references are made to The Royal Horticultural Society Colour Chart, 2001 Edition, except where general terms of ordinary dictionary significance are used.

Botanical classification: *Eryngium alpinum* 'White Star'.

Parentage: Naturally-occurring whole plant mutation of an unnamed selection of *Eryngium alpinum*, not patented.

Propagation:

*Type*.—By cuttings.

*Time to initiate roots*.—About 20 days at soil temperatures of about 14° C. to 16° C.

*Time to produce a rooted young plant*.—About 40 days at soil temperatures of about 14° C. to 16° C.

*Root description*.—Thick, fleshy; creamy white in color.

*Rooting habit*.—Moderately dense.

Plant description:

*Plant form/growth habit*.—Herbaceous perennial; upright plant habit; moderately vigorous growth habit; strong, thick stems.

*Plant height*.—About 64 cm.

*Plant diameter or spread*.—About 26.7 cm.

*Stem description*.—Length: About 48.1 cm. Diameter: About 9 mm. Internode length: About 6.8 cm. Aspect: Upright. Strength: Strong. Texture: Smooth, glabrous; longitudinally ridged. Color: Close to 193A to 193B; longitudinal stripes, close to 138B.

Foliage description:

*Arrangement*.—Alternate, simple.

*Length*.—About 9.1 cm.

*Width*.—About 9.3 cm.

*Shape*.—Lower leaves, orbicular; stem leaves, palmately lobed.

*Apex*.—Lower leaves, broadly acute; upper leaves, narrowly acute.

*Base*.—Hastate.

*Margin*.—Lower leaves, serrate; upper leaves, serrate to laciniate.

*Texture, upper and lower surfaces*.—Smooth, glabrous; somewhat leathery.

*Venation pattern*.—Palmatifid, reticulate.

*Color*.—Developing leaves, upper surface: Close to 137C and 138A. Developing leaves, lower surface: Between 143B and 144A. Fully expanded leaves, upper surface: Close to N137A to N137B; venation, lower leaves, close to 145C to 145D; venation, upper leaves, close to NN155C to NN155D. Fully expanded leaves, lower surface: Close to 146B to 146C; venation, close to 146A.

*Petioles*.—Length: About 2.7 cm. Diameter: About 5 mm. Texture, upper and lower surfaces: Smooth, glabrous. Color, upper and lower surfaces: Close to 14A.

Flower description:

*Flower arrangement and flowering habit*.—Single rotate flowers arranged on dense cylindrical flower heads; flowers sessile; inflorescences terminal or arising from leaf axils; freely flowering habit with usually about 500 flowers developing per inflorescence. Flowers face upright and outwardly.

*Fragrance*.—None detected.

*Natural flowering season*.—Plants of the new *Eryngium* begin flowering about ten months after planting and flower naturally from late spring throughout the summer in The Netherlands.

*Flower longevity*.—Flowers last about ten days on the plant and about ten days as a cut flower; flowers persistent.

*Inflorescence height, terminal inflorescences*.—About 8.3 cm.

*Inflorescence diameter, terminal inflorescences*.—About 14 cm.

*Flower diameter*.—About 5 mm.

*Flower length (depth)*.—About 8 mm.

*Flower bud*.—Shape: Elliptic. Length: About 7 mm. Diameter: About 2 mm. Color: Close to 137D; towards the base, close to 138D.

*Petals*.—Arrangement: Five petals in a single whorl. Length: About 4 mm. Width: About 0.5 mm. Shape: Spatulate. Apex: Rounded. Margin: Entire. Texture, upper and lower surfaces: Smooth, glabrous. Color: When opening, upper and lower surfaces: Close to 157D. Fully opened, upper and lower surfaces: Close to 157D.

*Sepals*.—Arrangement: Five sepals in a single whorl. Length: About 4 mm. Width: About 1.5 mm. Shape: Ovate. Apex: Acute. Base: Cuneate. Margin: Entire. Texture, upper and lower surfaces: Smooth, glabrous. Color, immature, upper and lower surfaces: Close to 138C. Color, mature, upper and lower surfaces: Close to 138C.

*Inflorescence bracts*.—Arrangement: About four rows of 80 bracts subtending the inflorescence. Length: About 5.1 cm to 8 cm. Width: About 2.3 cm to 4.8 cm. Shape: Obovate. Apex: Sharply apiculate. Base: Cuneate. Margin: Laciniate to sharply serrate. Texture, upper and lower surfaces: Smooth, glabrous. Color, upper surface: Close to 157C and 196D. Color, lower surface: Close to 191A to 191B.

*Peduncles*.—Length, terminal peduncles: About 16.3 cm. Diameter, terminal peduncles: About 7 mm. Angle: Main peduncle, erect; lateral peduncles, about 50° from vertical. Strength: Strong. Texture: Smooth, glabrous; longitudinally ridged. Color: Close to 157C.

*Reproductive organs*.—Stamens: Quantity/arrangement: About five per flower. Filament length: About 2 mm. Filament color: Close to 144C. Anther shape: Ovate. Anther length: About 1 mm. Anther color: Close to 144C. Pollen amount: Scarce. Pollen color: Close to 155A. Pistils: Quantity: About three per flower. Pistil length: About 3.2 mm. Style length: About 3.1 mm. Style color: Close to 155C. Stigma shape: Rounded. Stigma color: Close to 155C. Ovary color: Close to 145C.

*Fruits and seeds*.—Fruit and seed development have not been observed on plants of the new *Eryngium*.

Disease/pest resistance: Plants of the new *Eryngium* have not been shown to be resistant to pathogens and pests common to *Eryngium* plants.

Garden performance: Plants of the new *Eryngium* have exhibited good tolerance to rain and wind, have been observed to high temperatures of about 35° C. and to be hardy to USDA Hardiness Zone 6.

It is claimed:

1. A new and distinct *Eryngium* plant named 'White Star' as illustrated and described.

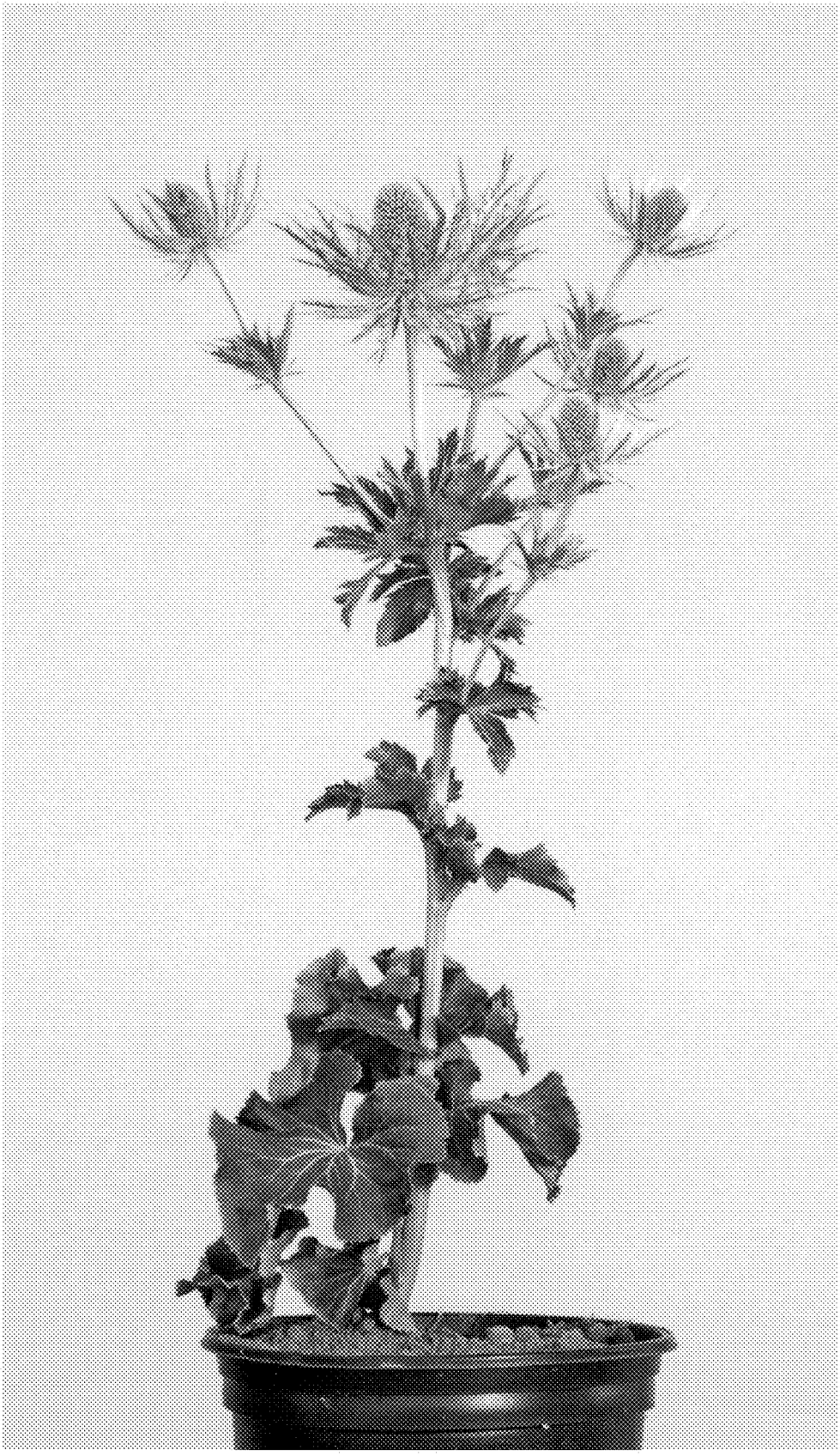

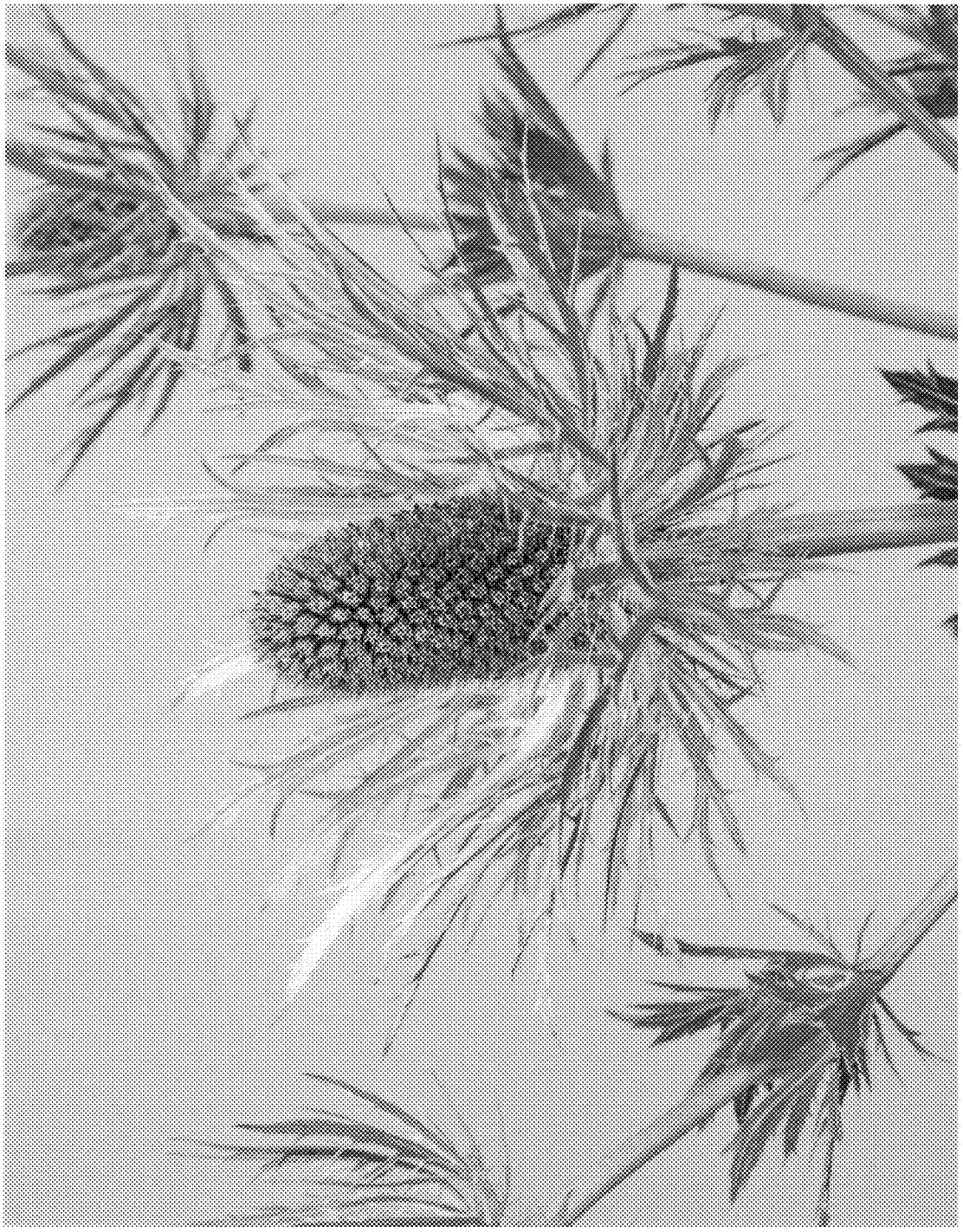

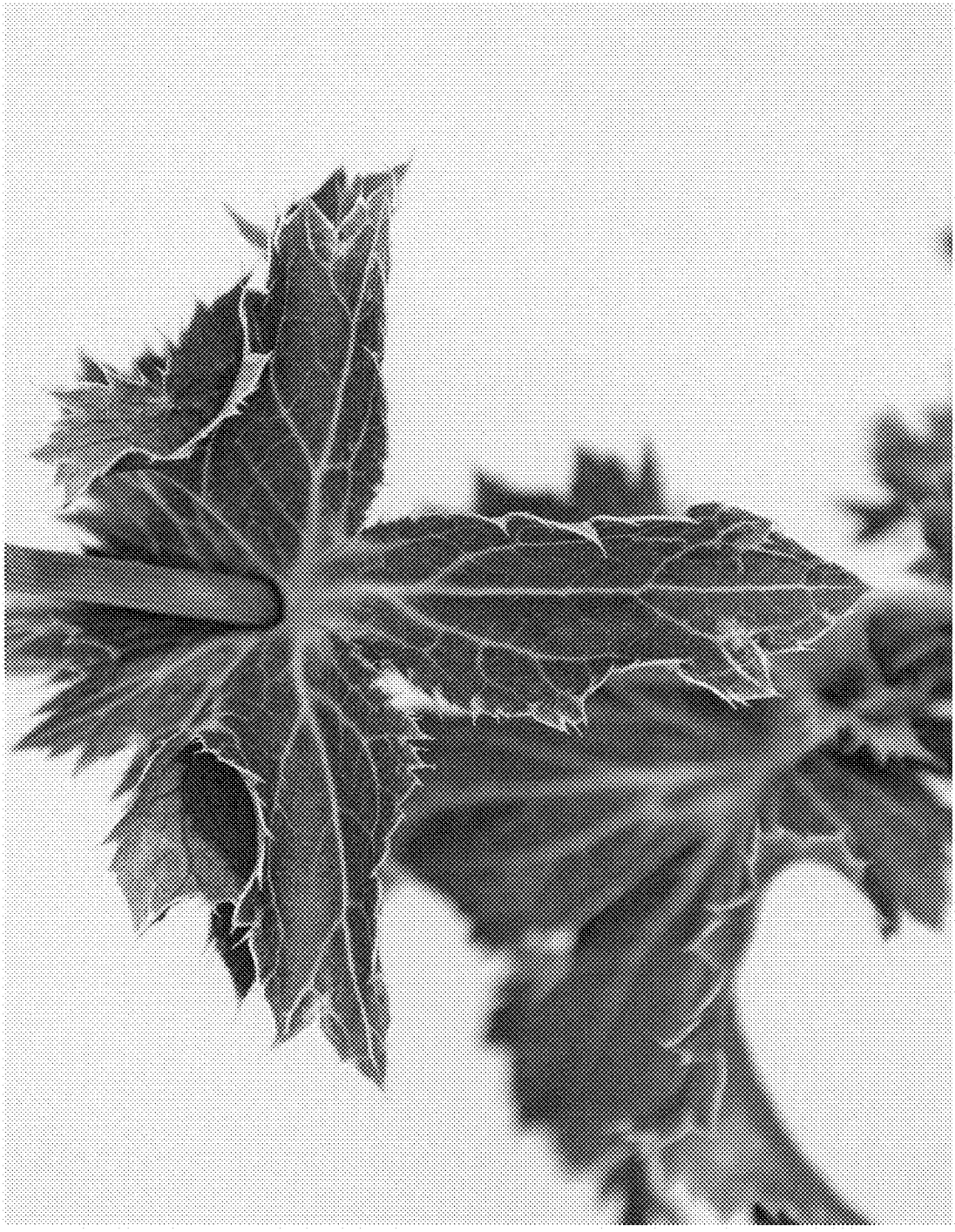

* * * * *